United States Patent [19]
Buckley et al.

[11] Patent Number: 5,352,218
[45] Date of Patent: Oct. 4, 1994

[54] VENOUS RESERVOIR BAG ASSEMBLY

[75] Inventors: John T. Buckley, Englewood; William D. Dalke, Aurora; Barry D. Reed, Lafayette; Joseph A. Scibona, Littleton; Rodger L. Stewart, Lafayette, all of Colo.

[73] Assignee: Cobe Laboratories, Inc., Lakewood, Colo.

[21] Appl. No.: 725,126

[22] Filed: Jul. 3, 1991

Related U.S. Application Data

[63] Continuation-in-part of Ser. No. 538,903, Jun. 15, 1990, abandoned.

[51] Int. Cl.⁵ ............................................. A61J 1/05
[52] U.S. Cl. .................................... 604/407; 604/403; 604/181; 604/408; 206/363; 222/65; 222/103
[58] Field of Search ............... 604/404, 408, 182, 181, 604/4, 5, 151, 153, 403, 407, 317, 322, 131; 206/363; 222/65, 66, 103; 248/95

[56] References Cited

U.S. PATENT DOCUMENTS

| | | | |
|---|---|---|---|
| 3,366,276 | 1/1968 | Fridley | 222/66 X |
| 3,642,047 | 2/1972 | Waage | 604/408 X |
| 3,734,351 | 5/1973 | Gaudin | 604/181 X |
| 3,942,529 | 3/1976 | Waage | 604/408 |
| 3,992,706 | 11/1976 | Tunney et al. | 222/66 X |
| 4,019,656 | 4/1977 | Spears | 222/103 |
| 4,019,707 | 4/1977 | Quinn et al. | 248/95 |
| 4,085,866 | 4/1978 | Fekl | 604/407 |
| 4,187,845 | 2/1980 | Droz | 604/182 X |
| 4,284,209 | 8/1981 | Barbour, Jr. | 222/130 X |
| 4,393,880 | 7/1983 | Taylor | 604/322 X |
| 4,496,354 | 1/1985 | Steer et al. | 604/322 |
| 4,976,851 | 12/1990 | Tanokura et al. | 222/103 X |
| 5,049,146 | 9/1991 | Bringham et al. | 604/4 |
| 5,061,236 | 10/1991 | Sutherland et al. | 604/4 |
| 5,078,677 | 1/1992 | Gentelia et al. | 604/317 X |

FOREIGN PATENT DOCUMENTS 7708421  2/1978  Netherlands ........................ 604/317

Primary Examiner—Robert A. Hafer
Assistant Examiner—Brian E. Hanlon

[57] ABSTRACT

A venous reservoir bag subassembly is provided which is adapted to cooperate with a mounting assembly having a bracket frame and a front plate reproducibly relatively movable to enable constant accurate blood volume readout, cooperating means between the subassembly and the mounting assembly to provide against unduly low blood volume, and angled conduit means cooperating with the bag and recesses in the subassembly and assembly to provide further failsafe against passage of the undesirable gas.

10 Claims, 4 Drawing Sheets

VENOUS RESERVOIR BAG ASSEMBLY

RELATED APPLICATIONS

This application is a continuation-in-part of our pending application Serial No. 07/538,903, filed Jun. 15, 1990 now abandoned by John T. Buckley; William D. Dalke; Barry D. Reed; Joseph A. Scibona; and Rodger L. Stewart under the title "Venous Reservoir Bag Assembly".

FIELD OF THE INVENTION

This invention relates to venous reservoir closed bag assemblies useful in cardiopulmonary bypass procedures.

BACKGROUND OF THE INVENTION

It is known in the prior art to use closed venous reservoir bags in cardiopulmonary bypass procedures. It is known also to use a woven mesh with 100 micron openings in such a bag to help remove air from blood flowing therethrough.

SUMMARY OF THE INVENTION

We have discovered that a venous reservoir bag is desirably mounted on a rigid plate, to provide a closed bag and bag plate subassembly. We have discovered further that this subassembly is desirably releasably latchable into a support assembly having a back support portion ("bracket frame") and a front portion ("front plate"), the portions being relatively movable in a constant space relationship to predeterminedly vary the instantaneous thickness (and thus volume) of the bag in a constant manner.

There is provided a closed bag system which is easy to use, with easy air handling and simplified accurate contents volume resolution.

PREFERRED EMBODIMENT

There is shown in the drawings the presently preferred embodiment of the invention, the structure and operation of which are now described.

DRAWINGS

STRUCTURE

Figure 1:
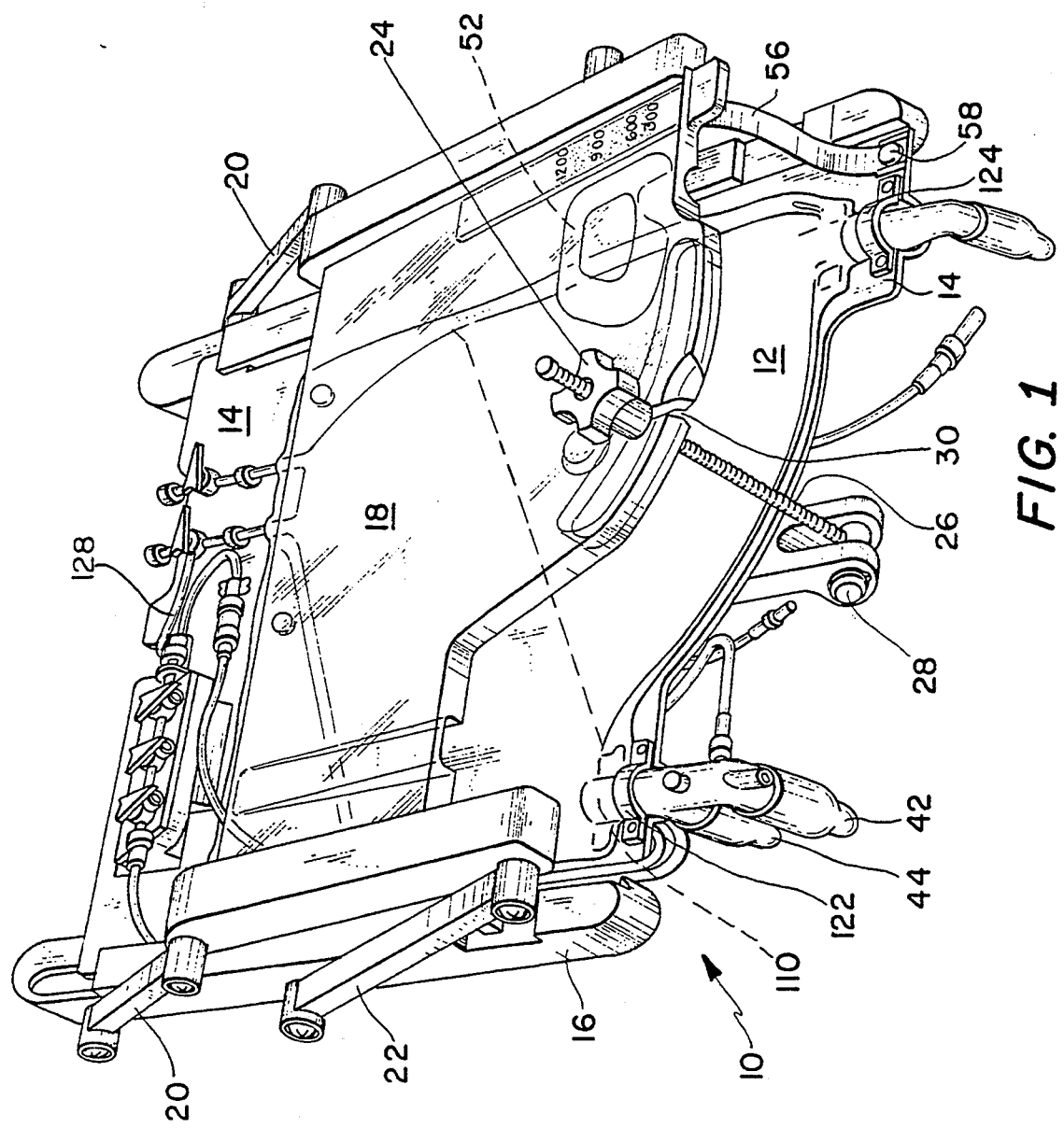
FIG. 1 is an isometric view of said embodiment, showing the front portion adjacent the back portion and the volume-limiting nut stop in one position.
Figure 2:
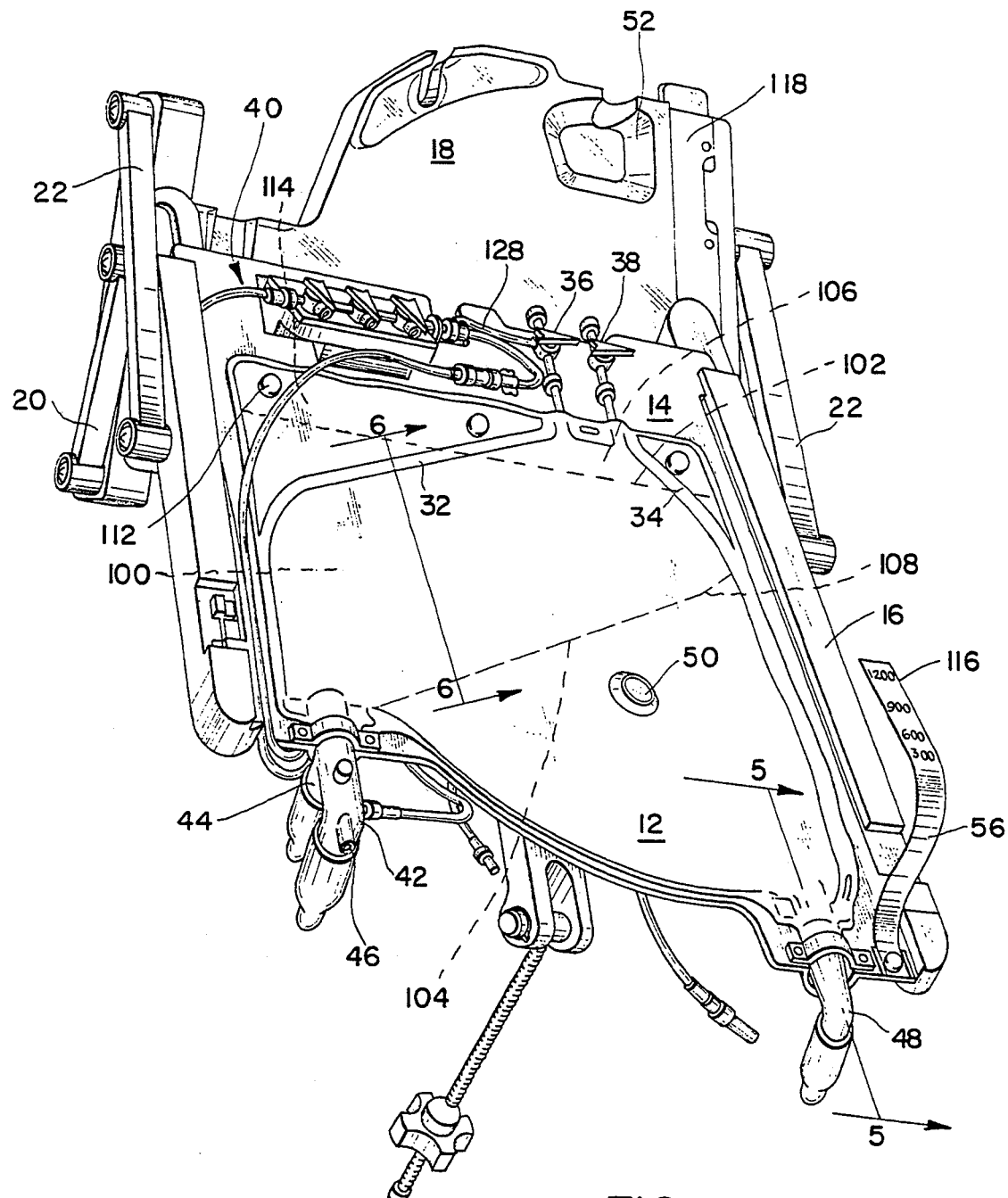
FIG. 2 is an isometric view of said embodiment showing the front portion moved away from the back portion.
Figure 3:
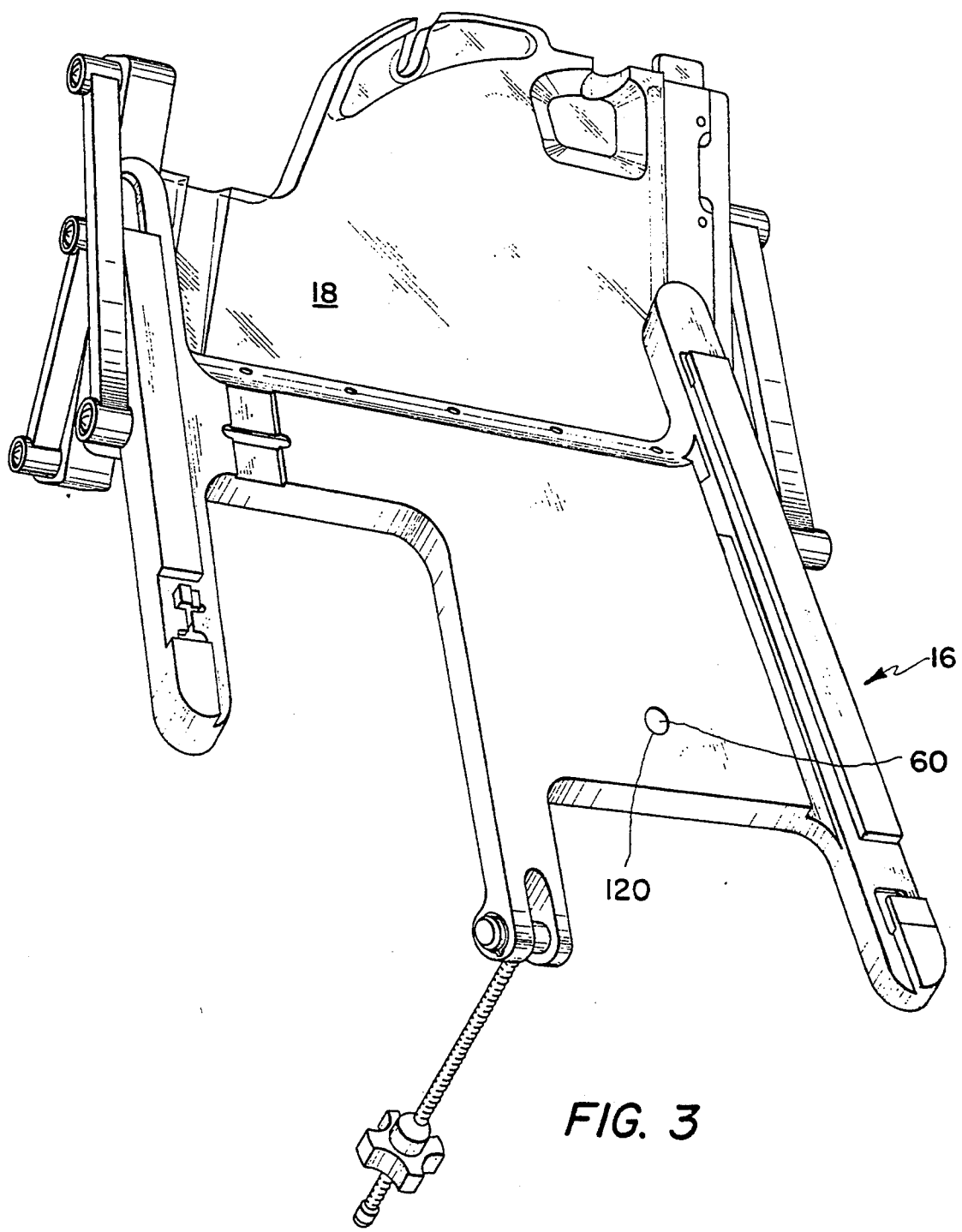
FIG. 3 is a view similar to FIG. 2, except with the bag and plate subassembly removed.
Figure 4:
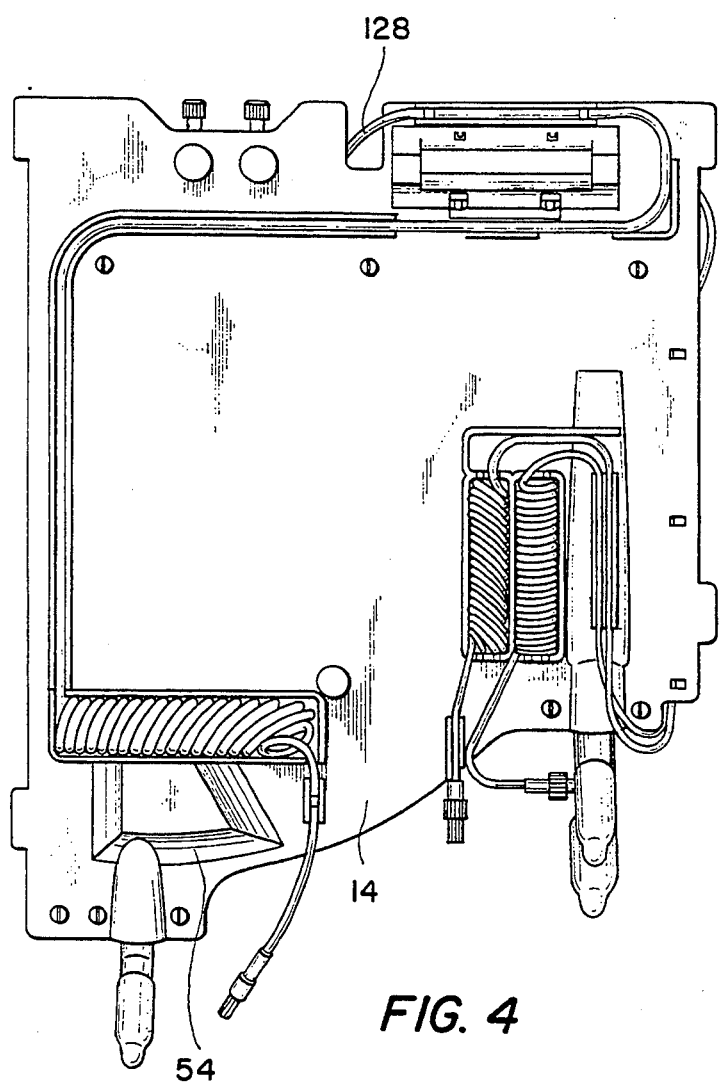
FIG. 4 is a rear elevation view of the bag plate of the embodiment.
Figure 5:
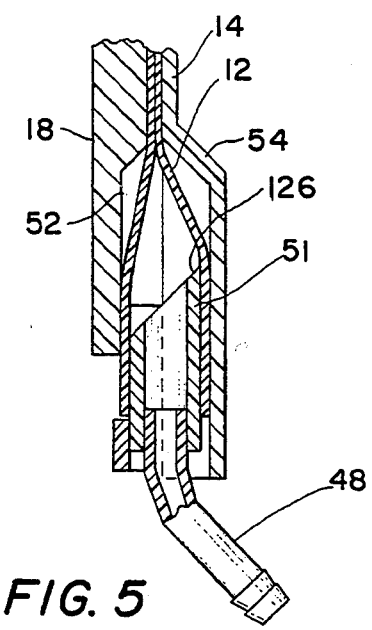
FIG. 5 is a sectional view taken at 5—5 of FIG. 2.
Figure 6:
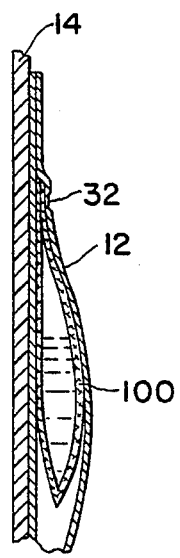
FIG. 6 is a sectional view taken at 6—6 of FIG. 2.

Referring now to FIG. 1, there is shown, in the preferred embodiment indicated generally at 10, the subassembly of closed 1200 ml. capacity bag 12 and bag plate 14 seated in the support assembly between its bracket frame 16 (as shown in FIG. 2) and its front plate 18.

Front plate 18, which weighs two pounds, is connected with bracket frame (back plate) 16 by a pair of shorter arms 20 and a pair of longer arms 22. Each arm 20 and 22 is pivotally secured toward its back end to bracket frame 16 and toward its front end to front plate 18, in a relationship such that at one travel extremity, as shown in FIG. 1, the plates 16 and 18 are nearly parallel, while at the other travel extremity, as shown in FIG. 2, plates 16 and 18 are widely separated. At the first mentioned travel extremity, plates 16 and 18 are spaced to permit 200 ml. of blood to enter before the volume of blood begins to move front plate 18.

The maximum distance between plates 16 and 18, and thus the maximum volume of bag 12, can be set by means of nut 24, which is threadedly carried by member 26 for uninterrupted continuously variable distance settings therealong, the member 26 being mounted for pivotal movement about pivot 28 carried by bracket frame 16, and engageable in slot 30 of front plate 18 to act as a stop therefor.

The bracket frame 16 is mounted (on pole means not shown) to support the bag and bag plate at an angle of 45°, or even more preferred, 55°, to the horizontal, the end of bag plate 14 at outlet 48, alongside the bottom of bag 12, being the lower end thereof.

Bag 12 is a flat "bag" formed of two layers of flexible vinyl sheet 114 RF welded around the periphery as at 32, 34. A woven polyester fabric (105 $\mu$ apertures) double layer element 100 between the vinyl layers aids in removing gas, for disposition then through outlets 36, 38. This fabric element is secured in the above-mentioned RF weld above which it extends to the pair of edges 102, and is folded along edge 104. There are two bypass regions around the screen within the bag. One is the area 106 at the very top of the screen in the region of the vent lines to outlets 36, 38. Heat seal 32 does not extend through fabric layers 100 here. This bypass 106 is to facilitate removal of air from both sides of the screen. The other screen bypass 108 is located at the rightmost part of the screen, farthest away from the venous inlet, a triangular portion of the double thickness of which is cut away. This is a safety bypass to minimize the possibility of pushing air through the screen in the extreme condition of running at very low reservoir volumes, and having a large amount of air collected in the screen without venting through the top of the bag. It also provides a bypass around the screen in the event the screen should become occluded.

Bag plate 14 carries bag 12 as well as the outlets 36, 38, and the blood gas sample system 40. Bag 12 includes as portions of it venous inlet 42, cardiotomy inlet 44, temperature probe 46, outlet 48, vent line 128 and magnet 50. Inlet 110, into which inlets 42 and 44 feed, is secured between the two layers of fabric element 100 within bag 12. Inlet tube 110 and outlet tube 51 are secured for immovability and thus strain relief with prevention of bag twisting in use by respectively clamps 22 and 124 secured to bag plate 14. The rigid bag plate 14 is of white plastic for contrast with blood level during use.

The outlet 48 connector is inserted into outlet tube 51 with an upper surface at 45° to the direction of blood flow and generally to the wall of bag 12. This provides positive shutoff when the reservoir is emptied of fluid if needed, the bag top surface moving appropriately against the angled surface. Premature shutoff is additionally prevented by pocket 52 in front plate 18 and pocket 54 in bag plate 14.

Pockets 52 and 54 keep the walls of bag 12 away from outlet tube 51 to prevent possible premature shutoff of blood flow.

Volume readout is provided by virtue of flexible tape 56, which bears indicia 116 as shown in the drawings, has its lower extremity 58 anchored in bag plate 14, and has its upper portions moving in a slot 118 in upper plate 18.

Insurance against drawing blood down too far and collapsing against the outlet tube 51, with possible air entrapment, is provided by the combination of magnet 50, mounted on the outer surface of bag 12 toward front plate 18, and normally open reed switch sensor 60, carried by bracket frame 16 in hole 120 just below magnet 50, protruding 0.100 inches above the surface of bracket frame 16 toward bag 12.

OPERATION

As blood is introduced through inlet 110, it rises first in a direction generally parallel with the surface of bag plate 14, which is in turn parallel with bracket frame 16. After 200 ml. has entered the volume within bag 12 defined by its heat sealed inner border and the inner surfaces of the bag portions now lying against bag plate 14 and front plate 18 is filled, so that further filling requires, and results in, movement of front plate 18, which in effect causes weighted front plate 18 to "float" on bag 12; during this stage, blood reservoir filling is in a direction basically perpendicular to the surface of bag plate 14. This double direction two-step approach to required blood reservoir filling provides consistent flow dynamics and air handling characteristics at all operating range blood levels. Also, reservoir fluid level is maintained in communication with vents 36, 38 throughout, and bag massage (with possible consequent release downstream of gas microemboli) is minimized. This filling action, plus the contrasting white plastic of bag plate 14, gives excellent low-volume (below 200 ml.) resolution.

The two bypasses, and the angled outlet tube inlet surface, contribute to this result.

Actually, the magnet 50 and sensor 60 ordinally by appropriate signal means when they reach a predetermined distance apart provide a predetermined lower limit on bag volume. The angled surface 126, which cooperates with the adjacent bag wall to provide complete cutoff without residual edge passages as when tubing is compressed between two flat surfaces, provides a secondary fail-safe in the event that the magnet and sensor somehow fail to do their job.

What is claimed is:

1. A body fluid reservoir bag support assembly comprising
   a bracket frame, said bracket frame including a back plate and a means for supporting said back plate at an acute angle to the horizontal, and
   a weighted front plate mounted for relative movement with respect to said back plate and to receive a fluid reservoir bag assembly including flexible bag between said front plate and said back plate, said front plate being mounted with respect to said back plate so as to be supported said flexible bag when filled and to move toward said back plate when the volume of said bag is decreasing and to move away from said back plate when the volume of said bag is increasing,
   in which said bracket frame and said front plate are connected by two pairs of arms, a first pair symmetrically oriented in parallel and relatively toward a first end of a carried bag plate having inlet and outlet tubes and a second pair symmetrically oriented in parallel and relatively toward the opposite end of said carried bag plate, each of said arms being pivotally mounted at one end on said bracket frame and at its other end on said front plate.

2. The assembly of claim 1 in which said arms of said first pair of longer than said arms of said second pair.

3. The assembly of claim 2 in which one of said bracket frame and front plate carries position sensing means and in which said position sensing means is a reed switch.

4. The assembly of claim 3 in which said reed switch is mounted in said bracket frame.

5. A body fluid reservoir assembly comprising
   a first plate,
   a second plate mounted for reproducible relative movement with respect to said first plate,
   a flexible bag having a variable volume and supported between said two plates such that there is relative movement between said two plates with respect to each other as a function of volume of said bag, and
   a flexible tape having volume indicia markings thereon and having one end fixed with respect to said first plate and another end that is a free end,
   the second plate having an indicator slot defined therein,
   said free end being slidably engaged within said indicator slot to visually indicate a volume of fluid contained in the bag as a function of the position of said first plate relative to said second plate.

6. The assembly of claim 5 wherein said first plate is a back plate, and said second plate is a front plate.

7. The assembly of claim 5 wherein said back plate is supported at an acute angle to the horizontal.

8. A body fluid reservoir assembly comprising
   a first plate,
   a second plate mounted for reproducible relative movement with respect to said first plate,
   a flexible bag having a variable volume and supported between said two plates,
   said bag having a flexible wall that moves with respect to said first plate as the volume of said bag changes,
   said flexible wall moving toward said first plate as volume decreases and moving away from said first plate as volume increases,
   a magnet mounted for movement with said flexible wall as the volume of said bag changes, said magnet is affixed to said flexible wall and
   a magnetic position sensing means mounted on said first plate at a location to be activated by said magnet when said magnet is at least as close to said first plate as a predetermined distance corresponding to a predetermined bag volume.

9. The assembly of claim 8 wherein said first plate is a back plate, and said second plate is a front plate.

10. The assembly of claim 8 wherein said magnetic position sensing means is a reed switch.

* * * * *

UNITED STATES PATENT AND TRADEMARK OFFICE
CERTIFICATE OF CORRECTION

PATENT NO. : 5,352,218
DATED : October 4, 1994
INVENTOR(S) : Buckley et al.

It is certified that error appears in the above-identified patent and that said Letters Patent is hereby corrected as shown below:

Column 2, line 54, "22" should be --122--;

Column 3, line 60, after "supported" insert --by--;

Column 4, line 12, the first "of" should be --are--;

and

Column 4, line 38, "5" should be --6--.

Signed and Sealed this

Seventh Day of February, 1995

Attest:

BRUCE LEHMAN

*Attesting Officer*     *Commissioner of Patents and Trademarks*